(12) United States Patent
Sussman

(10) Patent No.: US 9,278,027 B2
(45) Date of Patent: Mar. 8, 2016

(54) ROUNDED-END DEVICE, SYSTEM, AND METHOD FOR PREVENTING POSTERIOR CAPSULAR OPACIFICATION

(75) Inventor: Glenn Robert Sussman, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 208 days.

(21) Appl. No.: 13/544,124

(22) Filed: Jul. 9, 2012

(65) Prior Publication Data

US 2014/0012296 A1 Jan. 9, 2014

(51) Int. Cl.
*A61F 9/00* (2006.01)
*A61F 9/007* (2006.01)
*A61B 17/32* (2006.01)

(52) U.S. Cl.
CPC . *A61F 9/00745* (2013.01); *A61B 2017/320072* (2013.01); *A61B 2017/320096* (2013.01)

(58) Field of Classification Search
CPC ............... A61F 9/00745; A61B 2017/320072; A61B 2017/320096; A61B 2017/00336; B06B 3/00
USPC ........................................................ 606/107
See application file for complete search history.

(56) References Cited

U.S. PATENT DOCUMENTS

| | | | | |
|---|---|---|---|---|
| 3,809,093 A | * | 5/1974 | Abraham | 606/169 |
| 3,990,452 A | | 11/1976 | Murray et al. | |
| 4,869,715 A | * | 9/1989 | Sherburne | 604/22 |
| 5,084,012 A | * | 1/1992 | Kelman | 604/35 |
| 5,112,300 A | | 5/1992 | Ureche | |
| 5,199,943 A | * | 4/1993 | Wypych | 604/22 |
| 5,217,465 A | * | 6/1993 | Steppe | 606/107 |
| 5,269,297 A | * | 12/1993 | Weng et al. | 606/128 |
| 5,363,699 A | | 11/1994 | McCall | |
| 5,364,405 A | * | 11/1994 | Zaleski | 606/107 |
| 5,413,556 A | * | 5/1995 | Whittingham | 604/22 |
| 5,417,654 A | | 5/1995 | Kelman | |
| 5,718,677 A | * | 2/1998 | Capetan et al. | 604/35 |
| 6,176,857 B1 | | 1/2001 | Ashley | |
| 6,368,299 B1 | | 4/2002 | Cimino | |

(Continued)

FOREIGN PATENT DOCUMENTS

| | | |
|---|---|---|
| EP | 0269870 | 6/1988 |
| EP | 0352984 | 1/1990 |

(Continued)

OTHER PUBLICATIONS

International Search Report issued for PCT/US2013/046070, dated Sep. 10, 2013, 2 pgs.

(Continued)

*Primary Examiner* — Jonathan W Miles
*Assistant Examiner* — Chima Igboko
(74) *Attorney, Agent, or Firm* — Haynes and Boone, LLP

(57) ABSTRACT

Disclosed herein is an apparatus selectively attachable to an ultrasonic device to disrupt target cells from underlying tissue for treatment of an ocular condition, including a shaft, a coupling portion at an end of the shaft, and a cell disrupting end extending from a distal portion of the shaft. The shaft has a longitudinal axis and a first diameter. The coupling portion includes a connector portion and a hub configured to selectively couple to the ultrasonic device and impart ultrasonic vibration to the shaft. The cell disrupting end is solid and has a second diameter and a smooth, continuous, curved shape.

21 Claims, 4 Drawing Sheets

(56) References Cited

U.S. PATENT DOCUMENTS

| | | | |
|---|---|---|---|
| 6,491,670 B1* | 12/2002 | Toth et al. | 604/264 |
| 6,852,093 B1 | 2/2005 | Boukhny | |
| 6,902,558 B2* | 6/2005 | Laks | 604/521 |
| 7,204,820 B2* | 4/2007 | Akahoshi | 604/22 |
| 7,588,553 B2 | 9/2009 | Dewey | |
| 7,967,775 B2* | 6/2011 | Hong | 604/27 |
| 2005/0187513 A1* | 8/2005 | Rabiner et al. | 604/22 |
| 2005/0277898 A1 | 12/2005 | Dimalanta et al. | |
| 2006/0041220 A1 | 2/2006 | Boukhny et al. | |
| 2006/0100617 A1 | 5/2006 | Boukhny | |
| 2006/0189948 A1 | 8/2006 | Boukhny | |
| 2006/0253056 A1 | 11/2006 | Kadziauskas et al. | |
| 2007/0060926 A1 | 3/2007 | Escaf | |
| 2008/0167604 A1 | 7/2008 | Hong | |
| 2008/0281253 A1 | 11/2008 | Injev et al. | |
| 2009/0124960 A1* | 5/2009 | Mackool | 604/22 |
| 2009/0236938 A1* | 9/2009 | Bromfield | 310/323.19 |
| 2009/0306583 A1 | 12/2009 | Boukhny | |
| 2010/0036388 A1* | 2/2010 | Gomez | 606/107 |
| 2010/0121260 A1 | 5/2010 | Ghannoum et al. | |
| 2010/0160624 A1 | 6/2010 | Cunningham | |
| 2010/0168741 A1* | 7/2010 | Sanai et al. | 606/42 |
| 2010/0298851 A1* | 11/2010 | Nield | 606/169 |
| 2011/0082543 A1 | 4/2011 | Soll et al. | |
| 2011/0160624 A1 | 6/2011 | Babaev | |
| 2011/0278988 A1* | 11/2011 | Young et al. | 310/328 |
| 2011/0282335 A1 | 11/2011 | Jia et al. | |

FOREIGN PATENT DOCUMENTS

| | | |
|---|---|---|
| EP | 1464311 A1 | 10/2004 |
| JP | 49-36000 | 10/1974 |
| JP | 62-43692 | 9/1987 |
| JP | 2-68058 | 3/1990 |
| JP | 3-21186 | 3/1991 |
| JP | 7-507707 | 8/1994 |
| JP | 3165156 | 5/2001 |
| JP | 2002-177315 | 6/2002 |
| JP | 3325571 | 9/2002 |
| JP | 2004-358227 | 12/2004 |
| JP | 2010-500073 | 1/2010 |
| WO | WO 92/18075 | 10/1992 |
| WO | WO 93/16646 | 9/1993 |
| WO | WO 02/094346 | 11/2002 |
| WO | WO 2005/037086 | 4/2005 |
| WO | WO 2006/015131 | 2/2006 |

OTHER PUBLICATIONS

Extended European Search Report issued for EP 13816203.7, dated Jun. 3, 2015, 6 pgs.

Wolfram Wehner et al. "Capsular Cleaning to Remove Lens Epithelial Cells" Cataract & Refractive Surgery Today Europe, Mar. 2010, pp. 47-48.

Wolfram Wehner et al. "Prevention of Lens Capsule Opacification with ARC Neodymium:YAG Laser Photolysis After Phacoemulsification" Journal of Cataract & Refractive Surgery, vol. 36, Issue 6, Jun. 2010, pp. 881-884.

English Translation of Japanese Office Action issued for JP 2015-521625 dated Nov. 10, 2015, 4 pgs.

\* cited by examiner

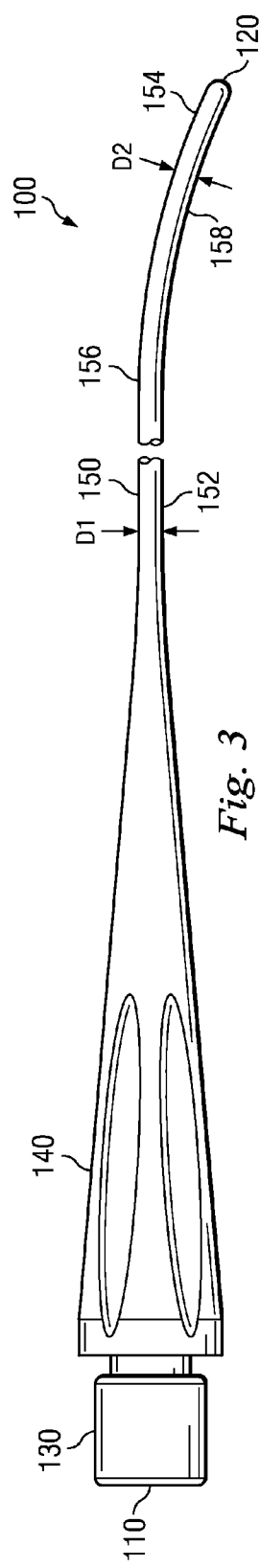
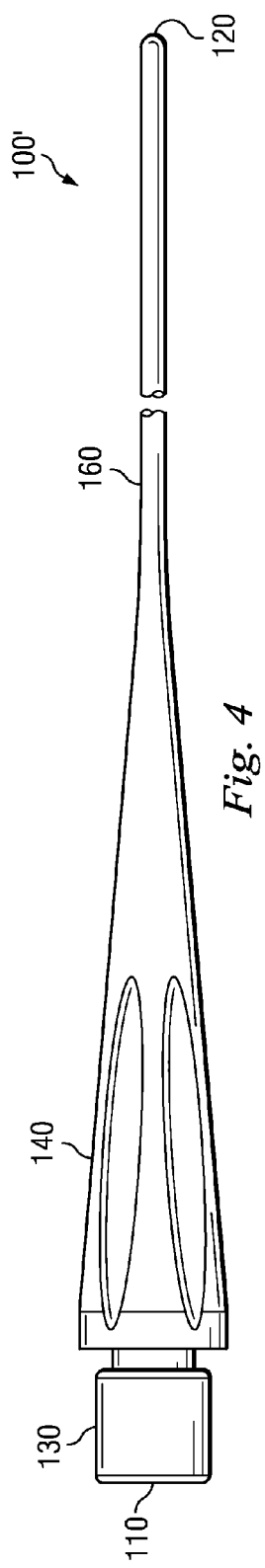
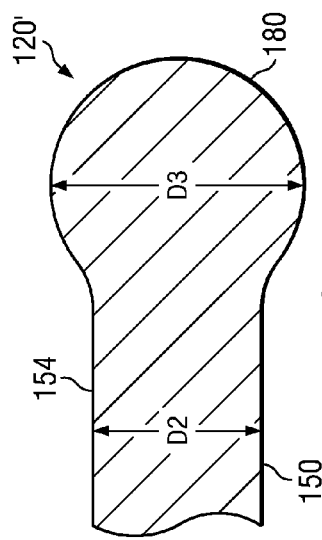
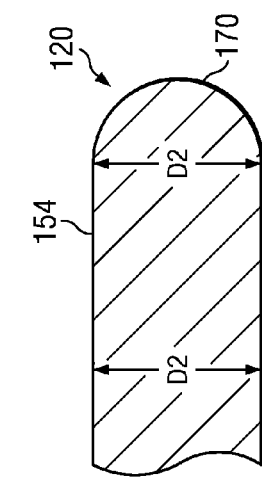
Fig. 3
Fig. 4
Fig. 5
Fig. 6

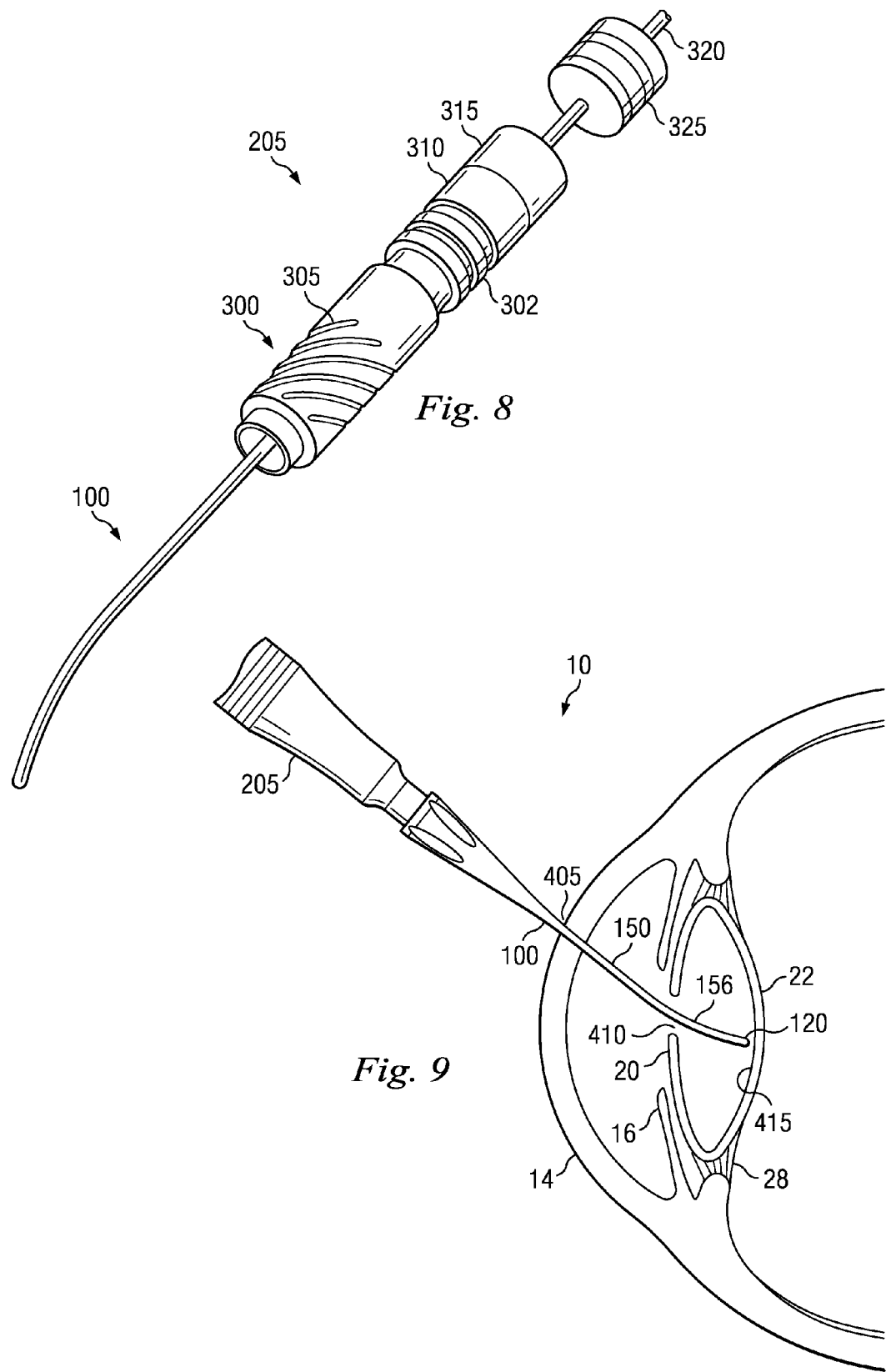

ROUNDED-END DEVICE, SYSTEM, AND METHOD FOR PREVENTING POSTERIOR CAPSULAR OPACIFICATION

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). Cataract extractions are among the most commonly performed operations in the world.

FIG. 1 is a diagram of an eye 10 showing some of the anatomical structures related to the surgical removal of cataracts and the implantation of IOLs. The eye 10 comprises an opacified lens 12, an optically clear cornea 14, and an iris 16. A lens capsule 18, located behind the iris 16 of the eye 10, contains the opacified lens 12, which is seated between an anterior capsule segment or anterior capsule 20 and a posterior capsular segment or posterior capsule 22. The anterior capsule 20 and the posterior capsule 22 meet at an equatorial region of the lens capsule 18. The eye 10 also comprises an anterior chamber 24 located in front of the iris 16 and a posterior chamber 26 located between the iris 16 and the lens capsule 18.

A common technique of cataract surgery is extracapsular cataract extraction ("ECCE"), which involves the creation of an incision near the outer edge of the cornea 14 and an opening in the anterior capsule 20 (i.e., an anterior capsulotomy) through which the opacified lens 12 is removed. The lens 12 can be removed by various known methods including phacoemulsification, in which ultrasonic energy is applied to the lens to break it into small pieces that are promptly aspirated from the lens capsule 18. Thus, with the exception of the portion of the anterior capsule 20 that is removed in order to gain access to the lens 12, the lens capsule 18 remains substantially intact throughout an ECCE. The intact posterior capsule 22 provides a support for the IOL and acts as a barrier to the vitreous humor within the posterior chamber 26. Following removal of the opacified lens 12, an artificial IOL is typically implanted within the lens capsule 18 through the opening in the anterior capsule 20 to mimic the transparency and refractive function of a healthy lens. Alternatively, a lens material may be injected to fill the lens capsule 18 and create an artificial "lens" in situ. The IOL may be acted on by the zonular forces exerted by a ciliary body 28 surrounding the periphery of the lens capsule 18. The ciliary body 28 anchors the IOL in place and facilitates accommodation, the process by which the eye 10 changes optical power to maintain a clear focus on an image as its distance varies.

A frequent complication of ECCE and other forms of cataract surgery is opacification of the posterior capsule 22. Posterior capsule opacification ("PCO") results from the migration of residual lens epithelial cells from the "equatorial" region of the lens toward the center of the posterior capsule 22. Subsequent to ECCE, the lens epithelial cells may proliferate between the IOL and the surface of the posterior capsule 22, leading to wrinkling and clouding of the normally clear posterior capsule 22. If clouding of the posterior lens capsule 22 occurs within the visual axis, then the patient will experience a decrease in visual acuity and may require additional surgery to correct the patient's vision.

A widely utilized procedure to clear the visual axis of PCO is Neodymium:Yttrium-Aluminum-Garnet ("Nd:YAG") laser capsulotomy, in which a laser beam is used to create an opening in the center of the cloudy posterior capsule. However, Nd:YAG laser capsulotomy exposes patients to the risk of severe complications that can lead to significant visual impairment or loss, such as retinal detachment, papillary block glaucoma, iris hemorrhage, uveitis/vitritis, and cystoid macula edema. Moreover, the laser energy is ordinarily directed though the IOL, which may damage the optics of the implant or disrupt its placement within the lens capsule. Also, a laser capsulotomy may compromise the accommodative ability of the lens implant. Accordingly, there exists a need to prevent the occurrence of PCO rather than treating PCO at a later date after implantation of an IOL. This is especially desirable for the new generation of IOLs (i.e., accommodating IOLs) that are capable of accommodating in response to ciliary body contraction and need an intact posterior capsule to optimally function.

Other attempts to prevent PCO have included constructing IOLs to include sharp posterior edges to provide a structural barrier to the migration of lens epithelial cells from the equatorial zone to the visual axis of the posterior capsule 22. However, such lenses are relatively expensive and may introduce complications of their own, such as capsular adhesions. Still other attempts to prevent PCO have included the introduction of various chemical agents into the lens capsule 18 to destroy the residual lens epithelial cells before they migrate between the IOL and the posterior capsule. However, the use of these agents has been limited by their cytotoxic effects on other cells within the eye.

There remains a need for a device, system, and method to reduce the need for PCO treatments and their associated costs by reducing the chance of PCO before implantation of an artificial IOL. The system and methods disclosed herein overcome one or more of the deficiencies of the prior art.

SUMMARY

In one exemplary aspect, the present disclosure is directed to an apparatus selectively attachable to an ultrasonic device to disrupt target cells from underlying tissue for treatment of an ocular condition, comprising a shaft, a coupling portion at an end of the shaft, and a cell disrupting end extending from a distal portion of the shaft. The shaft has a longitudinal axis and a first diameter. The coupling portion at an end of the shaft includes a connector portion and a hub configured to selectively couple to the ultrasonic device and impart ultrasonic vibration to the shaft. The cell disrupting end is solid and has a second diameter and a smooth, continuous, curved shape.

In another exemplary aspect, the present disclosure is directed to a system for disrupting target cells from underlying tissue, comprising an instrument tip and an ultrasonic device. The instrument tip comprises a shaft, a proximal end, and a distal end extending from a distal portion of the shaft. The shaft has a longitudinal axis and a first diameter. The proximal end includes a connector portion and a hub. The distal end is solid and has a second diameter and a smooth, continuous, curved shape. The ultrasonic device comprises an ultrasonic horn and a plurality of piezoelectric elements coupled to the ultrasonic horn. The ultrasonic horn is configured to couple to the hub at the proximal end of the instrument tip. The plurality of piezoelectric elements is configured to produce longitudinal motion of the instrument tip when excited at a resonant frequency.

In one aspect, the system includes an ultrasonic horn including a plurality of circumferential, helical slits sized and shaped to provide torsional movement to the instrument tip.

In another exemplary aspect, the present disclosure is directed to a method for disrupting target cells from underlying tissue, comprising: positioning an instrument tip having a solid, smooth, and curved distal end in proximity to the target cells; applying energy through an instrument tip having a rounded, solid distal end in the direction of the target cells; and disrupting the target cells without puncturing the underlying tissue by the application of energy through the instrument tip.

In one aspect, the method comprises applying energy through the instrument tip by applying ultrasonic energy through the instrument tip.

In another aspect, the method comprises disrupting target cells from underlying tissue, wherein the target cells are lens epithelial cells and surrounding substrate and the underlying tissue is a posterior capsular surface of an eye.

In another aspect, the method comprises disrupting target cells from underlying tissue, wherein the target cells are lens epithelial cells and surrounding substrate and the underlying tissue is an equatorial portion of a capsular surface of an eye.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 3 is a side view of the exemplary instrument tip shown in FIG. 2.

FIG. 4 is a side view of an exemplary instrument tip according to another embodiment consistent with the principles of the present disclosure.

FIG. 5 is a cross-sectional side view of an exemplary distal end according to one embodiment consistent with the principles of the present disclosure.

FIG. 6 is a cross-sectional side view of an exemplary distal end according to another embodiment consistent with the principles of the present disclosure.

FIG. 8 is a perspective view of the exemplary instrument tip shown in FIGS. 2 and 3 attached to the phacoemulsification handpiece of FIG. 7 without its outer shell.

FIG. 9 is a side view of the exemplary instrument tip shown in FIGS. 2 and 3 positioned within an eye according to the principles of the present disclosure.

DETAILED DESCRIPTION

Figure 1:
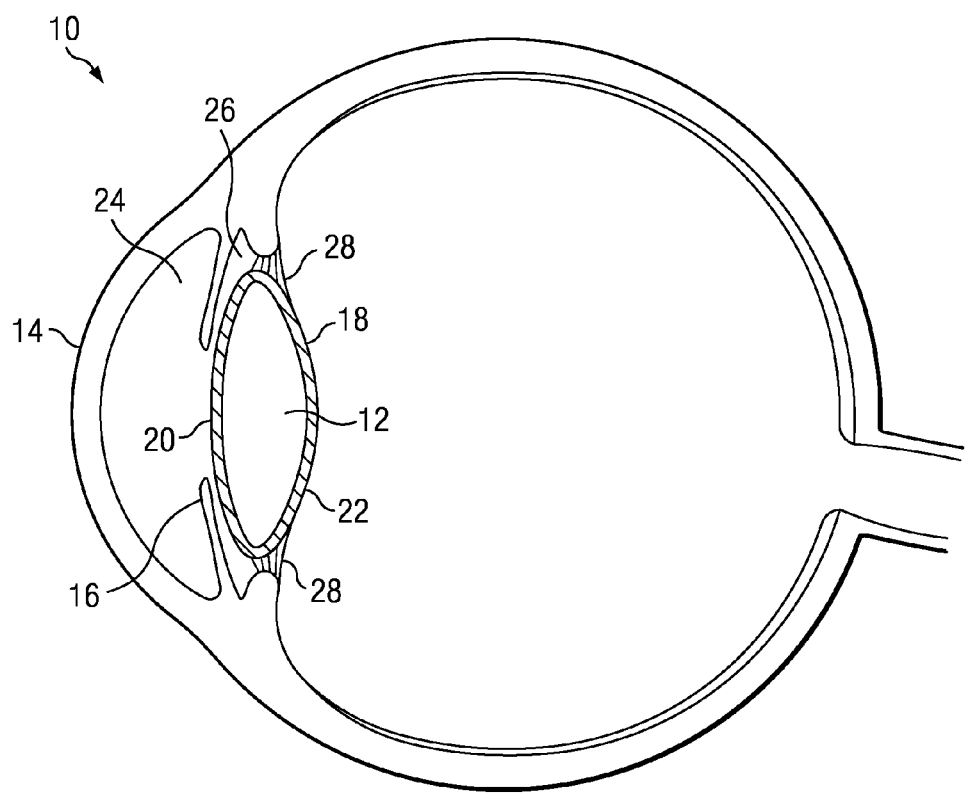
FIG. 1 is a diagram of a cross-sectional view of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for use in treating medical conditions, including ophthalmic conditions such as posterior capsular opacification ("PCO"). In some instances, embodiments of the present disclosure comprise instrument tips configured to reduce the occurrence of posterior capsular opacification after cataract extraction by selectively disrupting lens epithelial cells after extraction of an opacified lens and before insertion of an intraocular lens implant ("IOL"). "Disrupting" cells may include separating the cells from the underlying tissue and/or emulsifying/destroying the cells. In exemplary embodiments enclosed herein, the instrument tip lacks a lumen and comprises a solid, rounded distal end configured to deliver energy to residual lens epithelial cells on the posterior capsule and/or equatorial region of the lens capsule. In some instances, the tip is configured for use in a phacoemulsification system that delivers ultrasonic energy. The solid, rounded distal end provides an atraumatic tool to selectively disrupt lens epithelial cells on the capsule and prophylactically treat PCO without inadvertently aspirating, puncturing, or otherwise damaging the posterior capsule or other ocular cells.

Figure 2:
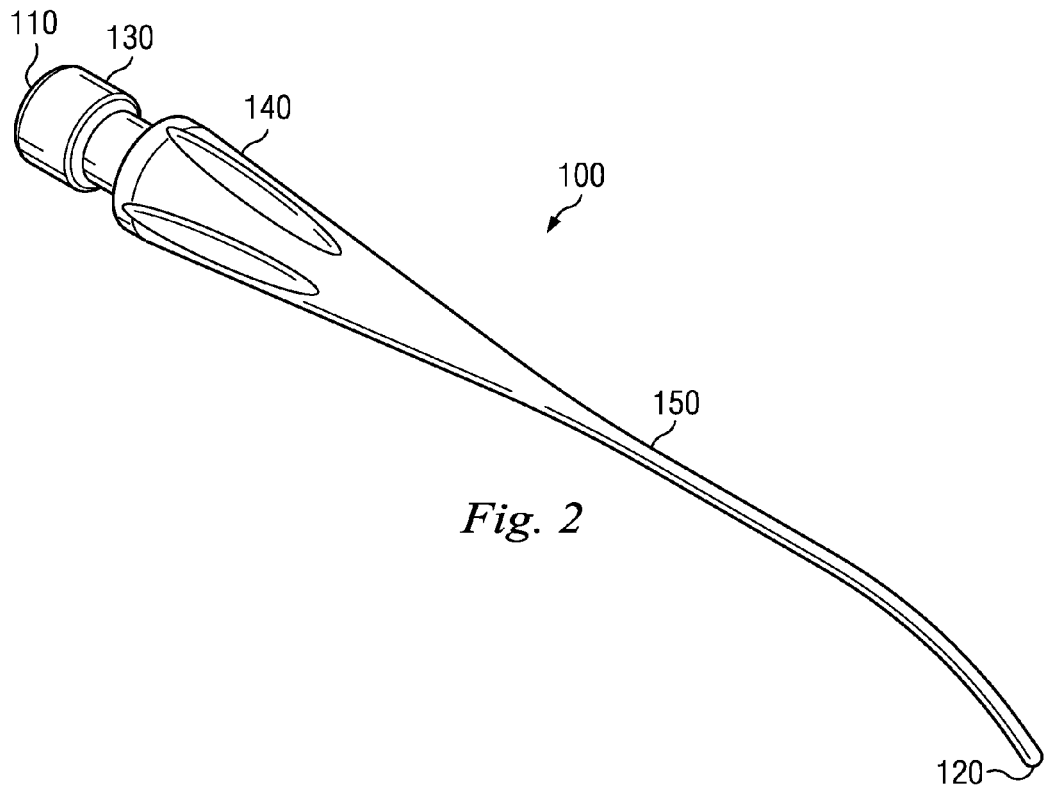
FIG. 2 is a perspective view of an exemplary instrument tip according to one embodiment consistent with the principles of the present disclosure.

FIG. 2 shows an instrument tip 100 according to one embodiment of the present disclosure. The instrument tip 100 extends from a coupling portion at a proximal end 110 to a cell disrupting end or distal end 120. The instrument tip 100 comprises a connector portion 130 at the proximal end 110, a hub 140, and a shaft 150 terminating at the distal end 120.

In the pictured embodiment, the connector portion 130 and the hub 140 are used to removably attach the instrument tip 100 to a phacoemulsification handpiece 205 (shown in FIG. 7) to couple ultrasonic energy to the instrument tip 100. The connector portion 130 and the hub 140 are shaped and configured to removably attach the instrument tip 100 to the phacoemulsification handpiece 205 using one or more of a threaded engagement, a snap-fit engagement, a frictional engagement, and/or any other mechanism for temporarily connecting instrument tip 100 to the phacoemulsification handpiece 205. In other embodiments, the connector portion 130 and the hub 140 are used to removably attach the instrument tip 100 to another type of surgical handpiece to couple another form of energy to the instrument tip 100. By way of non-limiting example, other forms of energy that may be coupled to the instrument tip 100 include laser energy, thermal energy, and electrical energy.

The hub 140 tapers toward the shaft 150, which comprises a solid, cylindrical component terminating in the rounded distal end 120. Representatively, but not by way of limitation, the entire exterior periphery of the shaft 150 is parallel to its length (i.e., the shaft does not appreciably taper laterally inwardly along its length). For example, as shown in FIG. 3, an external diameter D1 of a proximal portion 152 of the shaft 150 is substantially the same as an external diameter D2 of a distal portion 154 of the shaft 150. In other embodiments, the shaft 150 is tapered along its length such that D2 is less than D1. The shaft 150 includes a cylindrical outer surface 156, which is shaped and configured to be smooth and free of any sharp edges or points. In the embodiments disclosed herein, the external diameter D2 of the cylindrical outer surface 156 near the distal end 120 does not exceed a standard outer diameter of a conventional 19-gauge or 20-gauge phacoemulsification needle.

As shown in FIGS. 2 and 3, the shaft 150, comprising the proximal portion 152 and a distal, angled portion 158, is angled toward the distal end 120. The angle of the curvature of the shaft 150 may vary depending upon various characteristics, including, by way of non-limiting example, specific ocular characteristics, the specific application, and the desired surgical technique. However, as shown in FIG. 4, the shaft may be rectilinear in other embodiments. FIG. 4 illustrates an instrument tip 100', which is substantially similar to the instrument tip 100 except for the rectilinear shaft 160, which comprises a substantially straight, non-tapered, non-angled solid shaft that terminates in the rounded distal end 120.

FIG. 5 illustrates the distal end 120 of the instrument tip 100 shown in FIGS. 2-4. The distal end 120 comprises a rounded, hemispherical outer surface 170 that extends seamlessly from the cylindrical outer surface 156 of the shaft 150. The external diameter of the distal portion 154 of the shaft 150 remains constant toward the distal end 120, and the distal end 120 includes the same diameter D2 as the shaft 150. The outer surface 170 is shaped and configured to avoid or eliminate any surfaces coming to a sharp point or a sharp edge. Accordingly, the distal end 120 of the exemplary instrument tip 100 comprises a rounded, solid hemisphere without any sharp edges or points.

Thus, the instrument tip 100 includes a rounded, solid distal end 120 that minimizes inadvertent damage to ocular structures such as the lens capsule 18. Incidental contact of the distal end 120 to the capsule 18 or iris 16 of a patient's eye will not result in damage to these structures. Moreover, given that the distal end 120 is solid, smooth, and lacking any lumen or opening, incidental contact of the distal end 120 to the lens capsule 18 will not result in inadvertent aspiration and/or tearing of the capsule 18. The rounded, solid distal end 120 allows for the instrument tip 100 to come into contact with the structures of the eye 10 without unintentionally endangering the structural integrity of these structures.

In the illustrated embodiments shown in FIGS. 2-5, the distal end of the instrument tip 100 is described as hemispherical and rounded. In other embodiments, however, the distal end of the instrument tip 100 can have a generally curved shape, including round, spherical, ovoid, and any other smooth, continuously curved shape. For example, FIG. 6 illustrates a distal end 120' according to another embodiment of the present disclosure. The distal end 120' is substantially similar to the distal end 120 except for the differences described herein. The distal end 120' comprises a balled-end, solid knob with a smooth, semi-spherical outer surface 180. The instrument tip 100 smoothly transitions in shape and diameter from the distal portion 154 of the shaft 150 into the balled-end distal end 120'. The distal end 120' includes a diameter D3 that is larger than the diameter D2 of the distal portion 154 of the shaft 150.

The instrument tips described herein can be made from a variety of suitable materials without departing from the scope of the present disclosure. By way of non-limiting example, the instrument tips described herein can be made from titanium, stainless steel, alloys thereof, or any other suitable material capable of transmitting ultrasound energy. In some embodiments, the smooth, rounded outer surfaces (e.g., 156, 170, and/or 180) of the instrument tips disclosed herein are hardened to resist nicking, burring, and scuffing, all of which may cause sharpened edges or points. The outer surfaces may be hardened by applying hard surface coatings, annealing, or using other conventional hardening techniques.

The instrument tip 100 may have an overall length from the proximal end 110 to the distal end 120 of between 0.4 mm and 0.8 mm. Other lengths are also contemplated. The shaft 150 of the instrument tip 100 may be generally tubular and have a maximum external diameter of between 0.5 mm and 1.0 mm. Other diameters are also contemplated.

Figure 7:
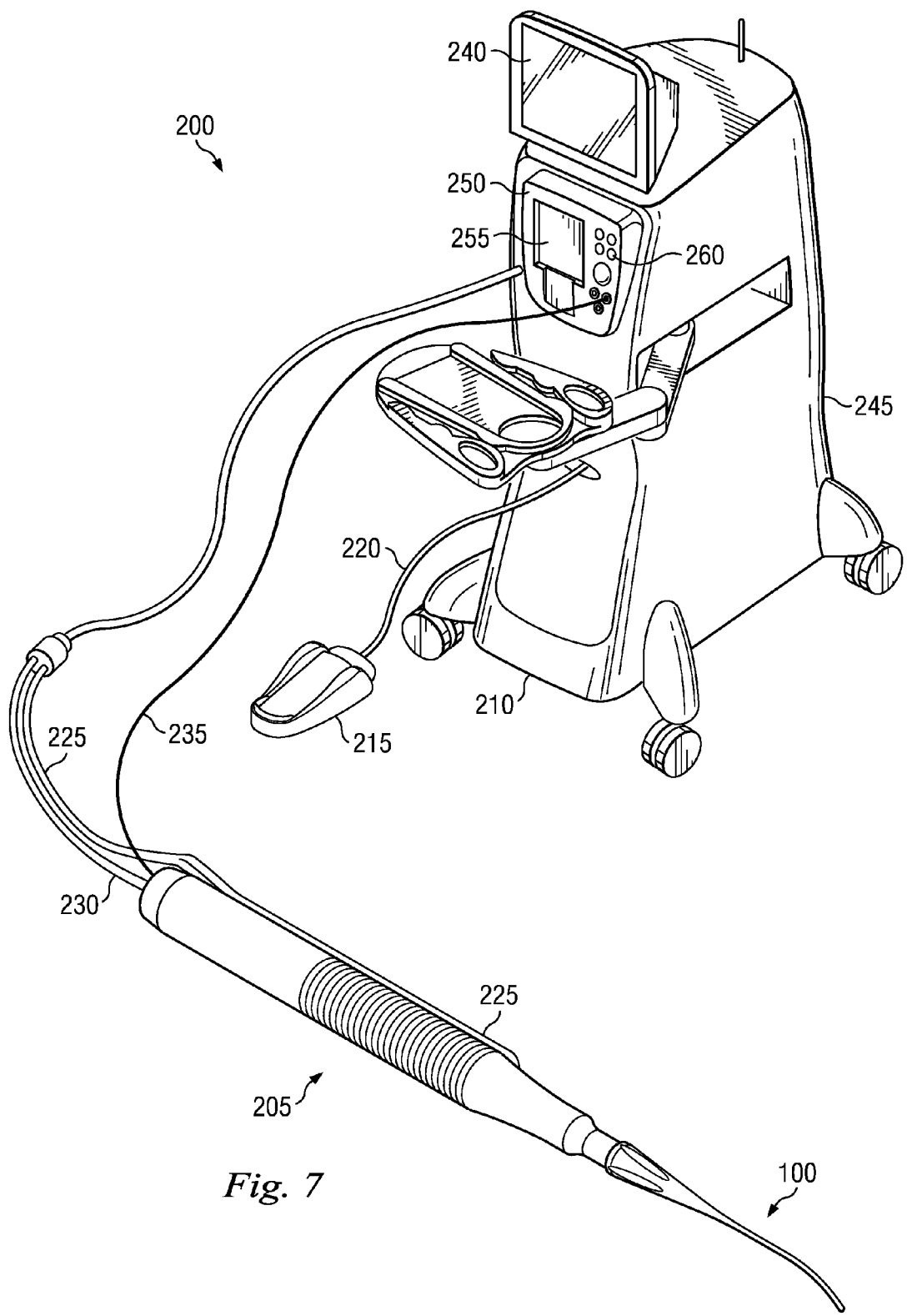
FIG. 7 is an illustration of a perspective view of a microsurgical system including a phacoemulsification handpiece according to one embodiment of the present disclosure.

FIG. 7 illustrates a microsurgical system 200 according to one embodiment of the present disclosure. Though the microsurgical system 200 shown in FIG. 7 is an ophthalmic microsurgical system, and in particular a phacoemulsification system, the microsurgical system may be any microsurgical system, including a system for performing otic, nasal, throat, maxillofacial, or other surgeries. In the pictured embodiment, the system 200 is capable of providing ultrasound power, irrigation fluid, and aspiration vacuum to an ultrasonic phacoemulsification handpiece 205 in an ophthalmic surgical procedure. The system 200 may also be capable of providing pneumatic drive pressure and aspiration vacuum to other surgical handpieces (e.g., by way of non-limiting example, a vitrectomy probe) and irrigation fluid to an irrigation cannula during an ophthalmic surgical procedure.

In the pictured embodiment, the system 200 includes a surgical console 210, the ultrasonic phacoemulsification handpiece 205, and a footswitch 215 connected to the surgical console 210 via a bi-directional bus or cable 220. In the pictured embodiment, the instrument tip 100 is attached to the handpiece 205. The handpiece 205 is connected to the surgical console 210 through an irrigation line 225 and an aspiration line 230. Flow through the lines 225 and 230 may be controlled by a user to perform the ophthalmic procedure (e.g., through the footswitch 215). In some embodiments, power is supplied to the handpiece 205 through an electrical cable 235.

The surgical console 210 comprises a graphic user interface 240 attached to a body 245 and a control console 250 disposed on a surface of the body 245. In some embodiments, the graphic user interface 240 has a liquid crystal display (LCD) with touch screen capability. In other embodiments, the graphic user interface 240 may include any of a variety of display devices, including by way of non-limiting example, LED displays, CRT's, and flat panel screens. The graphic user interface may include additional input devices or systems, including by way of non-limiting example, a keyboard, a mouse, a joystick, dials, buttons, among other input devices. The control console 250 includes a cassette receiving area 255 and a plurality of ports 260. A surgical cassette may be operatively coupled to the system 200 via the cassette receiving area 255 to manage the fluidics of the system 200 in a conventional manner. The bi-directional bus 220 sends signals in either direction between the surgical console 210 and the footswitch 215, and may be used to transmit power to the footswitch 215. In some embodiments, the surgical console 210 and the footswitch 215 communicate through a wireless connection.

The system 200 may include a microprocessor, random access memory (RAM), read only memory (ROM), input/output circuitry such as the bus 220, an audio output device, and other components of microsurgical systems well known to those in the art. A variety of peripheral devices may also be coupled to the system 200, such as storage devices (hard disk drive, CD ROM drive, etc.), printers, and other input/output devices.

During ophthalmic surgery, a series of handpieces may be coupled to the system 200, typically via conventional flexible plastic tubing fluidly coupled with the surgical cassette and/or electric cabling to operatively connect to the system 200 through one or more of the ports 260. Some exemplary handpieces that are utilized in anterior segment ophthalmic surgery include, for example, an irrigation handpiece, an irrigation/aspiration handpiece, an ultrasonic handpiece, and a diathermy handpiece. Exemplary handpieces that are utilized in posterior segment ophthalmic surgery include, by way of non-limiting example, an extrusion handpiece, an infusion cannula, a vitrectomy probe, microsurgical scissors, and a diathermy handpiece. In the pictured embodiment of FIG. 7, the phacoemulsification handpiece 205 is shown as one type of exemplary ultrasonic handpiece that may be coupled with the instrument tip 100. One example of a handpiece for a phacoemulsification procedure is described in the U.S. Patent Application Publication No. 2006/0041220, application Ser. No. 11/183,591, entitled "Ultrasound Handpiece," filed Jul. 18, 2005, which is hereby incorporated by reference in its entirety.

FIG. 8 illustrates a perspective view of the phacoemulsification handpiece 205 without its outer shell or casing. In particular, FIG. 8 shows an ultrasonic horn 300 according to one embodiment of the present disclosure attached to the exemplary instrument tip 100 shown in FIGS. 2 and 3. The ultrasonic horn 300 includes grooves 302 for sealing O-ring gaskets (not shown) and a plurality of helical grooves or slits 305, which are discussed in greater detail below. A plurality of ring-shaped piezoelectric elements 310 are held by a compression nut 315 against the ultrasonic horn 300. The piezoelectric elements 310 are polarized to produce longitudinal motion when excited at a relevant resonant frequency. An aspiration tube 320 may extend down the length of the handpiece 205 through the ultrasonic horn 300, the piezoelectric elements 310, the compression nut 315, and through a plug 325. The aspiration tube 320 allows for material to be aspirated during and after the phacoemulsification portion of an ECCE. By way of non-limiting example, a phacoemulsification needle may be attached to the handpiece 205 to break up a lens during a phacoemulsification procedure such that the lumen of the needle aligns with the aspiration tube 320. In the pictured embodiment, the solid, lumen-less instrument tip 100 may align with the aspiration tube 320, effectively blocking the aspiration tube 320. The plug 325 seals the outer shell or casing of the handpiece 205 fluid tight, allowing the handpiece 205 to be autoclaved without adversely affecting the piezoelectric elements 310.

As mentioned above, the ultrasonic horn 300 includes the plurality of helical slits 305, which produce torsional movement in the instrument tip 100 when the piezoelectric crystals are excited at a resonant frequency. The slits 305 provide suitable torsional movement of the instrument tip 100 and the ultrasonic horn 300 without compromising the longitudinal movement of the instrument tip 100 and the horn 300. The width of the slits 305 selected will depend upon the desired amount of torsional movement of the attached tip (e.g., the instrument tip 100). For example, in some embodiments, the width of the slits 305 ranges between 2% and 65% of the outside diameter of the ultrasonic horn 300. In some embodiments, the depth of the slits 305 ranges between 4% and 45% of the outside diameter of the ultrasonic horn 300. In some embodiments, the length of the slits 305 range between 8% and 75% of the length of the largest diameter of the ultrasonic horn 300. In the pictured embodiment, the slits 305 have a rounded profile or trough. In other embodiments, however, the slits have a flat or square-cut profile or trough. Movement of the instrument tip 100 caused by the slits 305 engaging fixed elements in the ultrasonic handpiece 205 may include a torsional component relative to an axis of rotation collinear with a centerline of the ultrasonic horn 300.

FIG. 9 illustrates the exemplary instrument tip 100 positioned within the eye 10 according to the principles of the present disclosure. In FIG. 9, the opacified lens 12 has been removed by an ECCE (e.g., by a phacoemulsification procedure) through an opening 405 in the cornea 14 and an opening 410 in the anterior capsule 20. As shown in FIG. 9, after extraction of the opacified lens 12, a surgeon can use the ultrasonic handpiece 205 coupled to the instrument tip 100 to disrupt the lens epithelial cells and surrounding substrate within the lens capsule 18 and prevent PCO. In particular, after aspirating the fragmented lens 12 from the lens capsule 18, the surgeon can remove the phacoemulsification tip from the ultrasonic handpiece 205 and replace it with the instrument tip 100. After the instrument tip 100 has been securely coupled to the ultrasonic handpiece 205, the surgeon may insert the instrument tip 100 through the openings 405, 410 in the cornea and the anterior capsule, respectively, to position the instrument tip 100 adjacent the posterior capsule 22. In some instances, the surgeon may position the instrument tip 100 adjacent the equatorial portion of the lens capsule. After adequately irrigating the lens capsule 18 to prevent its deflation and facilitate the use of ultrasonic energy, the surgeon can begin applying ultrasonic energy through the instrument tip 100 to disrupt and/or destroy the lens epithelial cells before the inception of PCO. In some embodiments, a portion or all of the instrument tip 100 may be positioned inside an irrigating sleeve (not shown) common to phacoemulsification procedures. In some embodiments, a fluid medium may be supplied prior to applying energy through the instrument tip 100 so that the fluid medium surrounds the instrument tip 100 and is adjacent to the target cells. For example, a flushing or irrigation solution may be injected into the surgical site through the small annular gap between the inside surface of the irrigating sleeve and the outside surface 156 of the instrument tip 100.

As shown in FIG. 9, the curved and solid nature of the distal end 120 of the instrument tip 100, as well as the significant surface area of the distal tip 120, enables the surgeon to work close to the lens capsule 18 and "polish" or clean a posterior capsular surface 415. The surgeon can apply ultrasonic energy through the instrument tip 100 toward the posterior capsular surface 415 (and/or the equatorial region of the lens capsule) to disrupt and/or destroy the lens epithelial cells. The instrument tip 100 can be ultrasonically vibrated along its longitudinal axis (e.g., within an irrigating sleeve) by the ultrasonic horn 305 (shown in FIG. 8), thereby emulsifying or otherwise disrupting the target cells from the posterior capsular surface 415. In some instances, the instrument tip 100 may be ultrasonically and torsionally vibrated along a small arc (e.g., +/−5 degrees). The torsional vibrations of the instrument tip 100 may result in lateral motions of the shaft 150 and the distal end 120. The oscillatory motion may include a side-to-side, back-and-forth torsional motion of the distal end 120 perpendicular to a central longitudinal axis of the shaft 150. In some embodiments, the instrument tip 100 may rotate back-and-forth at a rate of approximately 31 kHz. These arc degrees and rates of vibration are supplied for exemplary purposes only, and are not to be considered limiting. Various other rates of vibration and degrees of arcs are contemplated. For example, an arc of plus or minus 20 degrees and/or a rate of 10-60 kHz may be used.

In some instances, the surgeon may apply the ultrasonic energy in a sweeping, back- and forth motion by manually moving the ultrasonic handpiece 205. In other instances, the surgeon may apply the ultrasonic energy in a sweeping, torsional motion by employing the torsional movement provided by the slits 305 in the handpiece 205. In some instances, the surgeon may combine manual movements and torsional movements of the ultrasonic handpiece to treat the posterior capsule 22. By combining the application of ultrasonic energy and the movement (e.g., torsional and/or back-and-forth movement) of the instrument tip 100 adjacent the posterior capsular surface 415, the surgeon can disrupt and/or destroy the lens epithelial cells that may otherwise have proliferated across the posterior capsule 22 to cause PCO. Moreover, the surgeon can "polish" the posterior capsule 22 by disrupting the surrounding substrate material adjacent the lens epithelial cells, thereby preventing the migration of lens epithelial cells across the posterior capsule 22.

Following the disruption of the lens epithelial cells and the substrate, the surgeon may remove the instrument tip 100 from the eye 10 through the openings 405, 410. Aspiration is not necessary to remove the disrupted lens epithelial cells and surrounding substrate as these may be washed out of the lens capsule 18 with irrigation fluid through the openings 405, 410. Thereafter, the surgeon may implant an artificial IOL within the lens capsule 18 through the opening 410 in the anterior capsule 20 to mimic the transparency and refractive function of a healthy lens. Alternatively, a lens material may be injected to fill the lens capsule 18 and create an artificial "lens" in situ.

The ultrasonically-mediated disruption of lens epithelial cells using the instrument tip 100 may improve the stability of the lens capsule 18, and does not affect the ability of the lens capsule 18 to aid the accommodation process. In some instances, the lens capsule 18 may mold or shape an IOL and structurally contribute to control the refraction of the IOL. As mentioned above, the IOL may be acted on by the zonular forces exerted by the ciliary body 28 surrounding the periphery of the lens capsule 18. The ciliary body 28 anchors the IOL in place and facilitates accommodation, the process by which the eye 10 changes optical power to maintain a clear focus on an image as its distance varies. Thus, the devices, systems, and methods described herein supply a receptive environment for accommodative IOLs (e.g., IOLs that are configured to change focus and accommodate vision) by inhibiting PCO without sacrificing capsular compliance or integrity.

Embodiments in accordance with the present disclosure provide users with an atraumatic tool to selectively disrupt lens epithelial cells and surrounding substrate on the posterior capsule and prophylactically treat PCO to provide a stable lens capsule without inadvertently aspirating, puncturing, or otherwise damaging the posterior capsule or other ocular cells. Therefore, the embodiments of the present disclosure avoid the post-operative complications associated with posterior capsulotomy. Moreover, the embodiments of the present disclosure allow for the rapid and efficient disruption of lens epithelial cells before the implantation of an IOL, thereby avoiding the damage to the IOL that may arise during treatment of PCO after IOL implantation. In addition, the embodiments of the present disclosure allow for prophylactic treatment of PCO during the initial cataract extraction surgery, thereby reducing the number and cost of surgical procedures the patient may have otherwise had to undergo. Also, the embodiments of the present disclosure eliminate the need for a separate handpiece and/or surgical system to prevent PCO after removal of a lens by a conventional ECCE.

Embodiments in accordance with the present disclosure may be used in a variety of applications to selectively destroy cells without otherwise injuring the surrounding tissue. For example, but not by way of limitation, embodiments of the present disclosure may be utilized to remove surface cells from a variety of anatomical capsules and/or linings without rupturing the underlying capsule or lining. Some embodiments of the present disclosure may be utilized to destroy cells in a variety of anatomic organ systems such as, but not by way of limitation, the circulatory system, the excretory system, the digestive system, and the pulmonary system.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An apparatus to disrupt target cells from underlying tissue for treatment of an ocular condition, comprising:
   an ultrasonic device comprising:
      a horn; and
      an aspiration tube extending through the horn; and
   a first selectively attachable component configured to block the aspiration tube of the ultrasonic device when attached to the ultrasonic device, the first selectively attachable component comprising:
      a shaft having a longitudinal axis and a first diameter;
      a coupling portion at an end of the shaft including a connector portion and a hub configured to selectively couple to the ultrasonic device and impart ultrasonic vibration to the shaft; and
      a cell disrupting end extending from a distal portion of the shaft and having a second diameter, wherein the cell disrupting end is solid along the longitudinal axis and has a smooth, continuous, curved shape.

2. The apparatus of claim 1, wherein the first diameter and the second diameter are equal.

3. The apparatus of claim 2, wherein the cell disrupting end is shaped and configured as a rounded hemisphere.

4. The apparatus of claim 1, wherein the second diameter is greater than the first diameter.

5. The apparatus of claim 4, wherein the cell disrupting end is shaped and configured as a rounded, spherical knob extending from the distal portion of the shaft.

6. The apparatus of claim 1, wherein the connector portion and the hub are shaped and configured to couple the apparatus to an ultrasonic device by a coupling method selected from the group consisting of a threaded engagement, a snap-fit engagement, and a frictional engagement.

7. The apparatus of claim 1, wherein the distal portion of the shaft is angled such that a longitudinal axis of the distal portion is not parallel to the longitudinal axis of the shaft.

8. The apparatus of claim 1, further comprising: a second selectively attachable component comprising a phacoemulsification needle configured to engage with the aspiration tube of the ultrasonic device when attached to the ultrasonic device.

9. The apparatus of claim 1, wherein the horn includes:
   grooves for sealing O-ring gaskets; and
   a plurality of helical slits, the helical slits being configured to produce torsional movement when excited at a resonant frequency;
   wherein the ultrasonic device further comprises a plurality of ring-shaped piezoelectric elements held by a compression nut against the ultrasonic horn;
   wherein the aspiration tube further extends through the piezoelectric elements, and the compression nut;

wherein the first selectively attachable component is configured to align with the aspiration tube; and wherein the hub has a width greater than the shaft and tapers toward the shaft.

10. A system for disrupting target cells from underlying tissue, comprising:
- an instrument tip, comprising:
  - a shaft having a longitudinal axis and a first diameter;
  - a proximal end including a connector portion and a hub; and
  - a distal end extending from a distal portion of the shaft and having a second diameter, wherein the distal end is solid along the longitudinal axis and has a smooth, continuous, curved shape; and
- an ultrasonic device, comprising:
  - an ultrasonic horn configured to couple to the hub at the proximal end of the instrument tip, the horn comprising an aspiration tube extending therethrough; and
  - a plurality of piezoelectric elements coupled to the ultrasonic horn and configured to produce longitudinal motion of the instrument tip when excited at a resonant frequency;
- wherein the instrument tip is configured to block the aspiration tube when connected to the ultrasonic horn.

11. The system of claim 10, wherein the wherein the first diameter and the second diameter are equal.

12. The system of claim 11, wherein the distal end of the instrument tip is shaped and configured as a rounded hemisphere.

13. The system of claim 10, wherein the second diameter is greater than the first diameter.

14. The system of claim 13, wherein the distal end of the instrument tip is shaped and configured as a rounded, spherical knob extending from the distal portion of the shaft.

15. The system of claim 10, wherein the connector portion and the hub are shaped and configured to couple the apparatus to the ultrasonic device by any coupling method selected from the group consisting of a threaded engagement, a snap-fit engagement, and a frictional engagement.

16. The system of claim 10, wherein the distal portion of the shaft of the instrument tip is angled such that a longitudinal axis of the distal portion is not parallel to the longitudinal axis of the shaft.

17. An apparatus to disrupt target cells from underlying tissue for treatment of an ocular condition, comprising:
- an ultrasonic device comprising an ultrasonic horn and an aspiration tube; and
- a selectively attachable component comprising:
  - a shaft having a longitudinal axis and a first diameter;
  - a coupling portion at an end of the shaft including a connector portion and a hub configured to selectively couple to the ultrasonic device and impart ultrasonic vibration to the shaft; and
  - a cell disrupting end extending from a distal portion of the shaft and having a second diameter, wherein the cell disrupting end is lumen-less and has a smooth, continuous, curved shape;
- wherein the selectively attachable component is configured to block the aspiration tube when connected to the ultrasonic device.

18. The apparatus of claim 17, wherein the first diameter and the second diameter are equal.

19. The apparatus of claim 18, wherein the cell disrupting end is shaped and configured as a rounded hemisphere.

20. The apparatus of claim 17, wherein the first diameter is smaller than the second diameter.

21. The apparatus of claim 20, wherein the cell disrupting end is shaped and configured as a rounded, spherical knob extending from the distal portion of the shaft.

* * * * *